US009226845B2

(12) United States Patent
Troncoso

(10) Patent No.: US 9,226,845 B2
(45) Date of Patent: Jan. 5, 2016

(54) POSTURE RETAINING BACK BRACE, BACKPACK STRUCTURAL SUPPORT OR BODY GARMENT

(76) Inventor: Victoria Troncoso, Scottsdale, AZ (US)

(*) Notice: Subject to any disclaimer, the term of this patent is extended or adjusted under 35 U.S.C. 154(b) by 31 days.

(21) Appl. No.: 13/460,925

(22) Filed: May 1, 2012

(65) Prior Publication Data

US 2013/0296756 A1 Nov. 7, 2013

(51) Int. Cl.
*A61F 5/02* (2006.01)
*A61F 5/00* (2006.01)
*A41D 13/05* (2006.01)

(52) U.S. Cl.
CPC . *A61F 5/026* (2013.01); *A61F 5/02* (2013.01); *A41D 13/0512* (2013.01); *A61F 5/00* (2013.01)

(58) Field of Classification Search
CPC .......... A61G 5/00; A61G 5/02; A61G 5/026; A41D 13/05; A41D 13/0512; A41D 13/0518; A41D 13/0531
USPC ........... 602/19; 128/874–876; 2/92, 459, 461, 2/462
See application file for complete search history.

(56) References Cited

U.S. PATENT DOCUMENTS

| | | |
|---|---|---|
| 224,784 A | 2/1880 | Johnstone |
| 245,655 A | 8/1881 | Phelp |
| 317,474 A | 5/1885 | Strouse |
| 369,803 A | 9/1887 | McComber |
| 496,816 A | 5/1893 | Corker |
| 770,752 A | 9/1904 | Hull |
| 880,904 A | 3/1908 | Mueller et al. |
| 1,129,515 A | 2/1915 | Perry |
| 2,477,792 A | 8/1949 | Fratianni |
| 2,591,462 A | 4/1952 | Mungo |
| 2,672,613 A | 3/1954 | Popp |
| 2,752,601 A | 7/1956 | Gluckin |
| 2,782,416 A | 2/1957 | Ginsburg |
| 3,008,468 A | 11/1961 | Williams |
| 3,027,898 A | 4/1962 | Williams |
| 3,499,441 A * | 3/1970 | Hall ............................... 602/19 |
| 3,856,004 A | 12/1974 | Cox |
| 3,906,944 A | 9/1975 | Christen |
| 4,459,979 A | 7/1984 | Lewis, Jr. |
| 4,894,868 A | 1/1990 | Christopher |
| 5,116,306 A * | 5/1992 | Zander ........................... 602/19 |
| 5,135,470 A | 8/1992 | Reeves |

(Continued)

FOREIGN PATENT DOCUMENTS

FR 569318 A 4/1924

*Primary Examiner* — Alireza Nia
*Assistant Examiner* — Keri J Nelson
(74) *Attorney, Agent, or Firm* — Dinsmore & Shohl LLP; Allen M. Krass

(57) ABSTRACT

A posture support system, which may alternatively act as a structural support for a backpack and/or be incorporated in a body garment or undergarment, employs a pair of contoured cap sleeves which cradle the humeral heads so as to extend over the scapulas and down over the humerus. The forward end extends as a strap under one of the armpits and connects at its end to the top of a vertically extending central strap extending over the spine. The central strap connects to a waist encircling lumbar support strap. The posterior strap-like ends of the shoulder caps extend over the back and also connect to the top of the spinal strap. By use of adjustable connections to a central disk at the top of the back strap and elastic fabrics in the straps, the shoulders are pulled rearwardly and downwardly so that the body weight is supported over the hips.

10 Claims, 4 Drawing Sheets

(56) References Cited

U.S. PATENT DOCUMENTS

| | | |
|---|---|---|
| 5,184,764 A | 2/1993 | Orovan et al. |
| 5,256,135 A | 10/1993 | Avihod |
| 5,319,806 A | 6/1994 | Hermann et al. |
| 5,529,229 A | 6/1996 | Fier |
| 5,586,705 A | 12/1996 | Leonard |
| 5,823,851 A | 10/1998 | Dicker |
| 5,950,628 A | 9/1999 | Dunfee |
| 6,120,213 A | 9/2000 | Stinton |
| 6,190,342 B1 | 2/2001 | Taylor |
| 6,280,287 B1 | 8/2001 | Keith et al. |
| 6,295,655 B1 | 10/2001 | Johe |
| 6,302,761 B1 | 10/2001 | Wrenn |
| 6,315,747 B1 | 11/2001 | Toole |
| 6,336,458 B1 | 1/2002 | Nafziger |
| 6,386,944 B2 | 5/2002 | Keith et al. |
| 6,421,833 B2 | 7/2002 | Khanamirian et al. |
| 6,440,094 B1 | 8/2002 | Maas |
| 6,460,746 B1 | 10/2002 | Amram |
| 6,540,707 B1 | 4/2003 | Stark et al. |
| 6,676,617 B1 | 1/2004 | Miller |
| 6,709,411 B1 | 3/2004 | Olinger |
| 6,936,021 B1 | 8/2005 | Smith |
| 6,991,611 B2 | 1/2006 | Rhee |
| 7,374,523 B2 | 5/2008 | Weir et al. |
| 7,578,798 B2 | 8/2009 | Rhee |
| 7,654,972 B2 | 2/2010 | Alleyne |
| 7,901,371 B1 | 3/2011 | Vayntraub |
| 8,047,893 B2 | 11/2011 | Fenske |
| 8,808,212 B1 * | 8/2014 | Redmond ............... A61F 5/026 128/846 |
| 2002/0052568 A1 | 5/2002 | Houser et al. |
| 2005/0197607 A1 | 9/2005 | Brown |
| 2006/0064045 A1 | 3/2006 | Khavari |
| 2008/0208089 A1 * | 8/2008 | Newkirk et al. ................ 602/19 |
| 2009/0126084 A1 | 5/2009 | Fenske |

* cited by examiner

POSTURE RETAINING BACK BRACE, BACKPACK STRUCTURAL SUPPORT OR BODY GARMENT

FIELD OF THE INVENTION

This invention relates to a posture-improving support system comprising a series of body straps and connecting shoulder caps and more particularly to such a system which may be used to improve posture, to act as a support for a backpack, or may be built into a garment or undergarment.

BACKGROUND OF THE INVENTION

Prior art back braces or backpack structural supports typically include straps that extend over the wearer's shoulders midway between the neck and the top of the arm bone (humerus). This contact on the trapezius muscle results in chronic straining of the trapezius and the levator scapulae muscles. The straining of these muscles causes spasms and eventually weakening of the muscle between the shoulder blades, the rhomboid and teres muscles, whose job it is to keep the shoulder blades flat on the back. This imbalance of muscle tensions creates a worsening of stooped shoulder, head forward posture, rather than improving posture, and often creating pain, headaches and diminished breathing capacity. In order to correct stooped shoulder/head forward posture, it is necessary to draw the shoulders rearwardly and downwardly. If this support is to be used for a backpack, it is necessary to distribute the weight to the hips.

SUMMARY OF THE INVENTION

The present invention is accordingly directed toward a posture support brace which a user may wear to resiliently bias the user's shoulders in a rearwardly and downwardly direction to improve posture. Alternatively, the brace may be formed integrally with a garment or undergarment so that the user donning the garment/undergarment will properly apply the brace to the user's body. In another alternative, the brace may provide a support for a backpack or the like so that the weight of the backpack is properly supported on the user's hips and the user's shoulders are simultaneously drawn rearwardly and downwardly to center the user's weight over the spine and thus improve the user's posture.

In each of these forms of the invention the brace comprises a pair of contoured cap sleeves shaped to rest in a position centered over the two acromio-clavicular joints of the user's shoulders. The cap sleeves are contoured to have two short sections which connect to each other at an obtuse internal angle in the range of about 100-160 degrees. One of these sections of the contoured cap is adapted to extend over the far end of the user's clavicle and the other section extends for a short distance down the top of the arm bone or humerus. The lower ends of the anterior sections of each of the two caps extend as straps under the respective armpits (axillas) of the user and the lower ends of the posterior sections of each cap extend as straps over the clavicle.

Both ends of each cap are secured to the top end of an elastic vertical back strap extending over the user's spine from a top end below the user's shoulders to a lower end at a waist strap adapted to rest on the user's iliac crests. The backpack support system relies on the downward pull of the elastic medial spine strap which is joined to the waist strap at its lower end to provide tension to the shoulder caps.

The straps of the brace are preferably formed of a fabric having elasticity in the range of about 0.02-0.15 Young's modulus. The cap sleeves are also formed of an elastic fabric having a Young's modulus toward the higher end of that range.

The elastic straps forming the lower ends of the posterior sections of each shoulder cap extend over the back and are attached to the top end of the vertical spinal strap so that they are under tension. The elastic straps forming the lower ends of the anterior sections of each shoulder cap extend under the armpits and across the back with their ends also attached to the top end of the vertical spine strap. The tension on these elastic straps draws the shoulders downwardly and rearwardly.

The ends of these shoulder cap sleeve straps may be secured to the top end of the spinal strap by a connection such as a hook-and-loop fastener and/or an adjustable clip which may be adjusted to impose tension on the straps and also adjust angularly. In the version of the brace that is incorporated in a garment, the act of donning the garment stretches these straps to exert the rearward and downward forces on the shoulders. In the version of the back brace in which the brace is integrally formed with a backpack or connected to a backpack by separable fasteners, the weight of the backpack imposes tensile forces on the straps extending from the lower ends of the contoured cap sleeves to urge the shoulders rearwardly and downwardly.

The present invention thus provides a support system that bears on the user's arms at the acromio-clavicular joints in a comfortable manner and contacts the deltoid muscles, avoiding the forces imposed on the shoulders by prior art back support systems which contact the wearer midway between the neck and the top of the arm bone. Use of the present back brace will thus result in an upright, normal spinal alignment.

When the present back support system is incorporated in children's backpacks, they may be custom fitted so that the vertical spinal covering strap connects to the lumbar waist support to provide even weight distribution to the hips.

When incorporated in backpacks for adults, the present invention provides for adjustment of the support structure to different back sizes. In versions of the backpack for heavy-duty packing, the contoured cap sleeves may be made of material having a high Young's modulus so as to be substantially inelastic.

BRIEF DESCRIPTION OF THE DRAWINGS

Other objects, advantages, and applications of the present invention will be made clear by the following detailed description of preferred embodiments of the invention. The description makes reference to the accompanying drawings in which.

DETAILED DESCRIPTION OF PREFERRED EMBODIMENTS OF THE INVENTION

Figure 1:
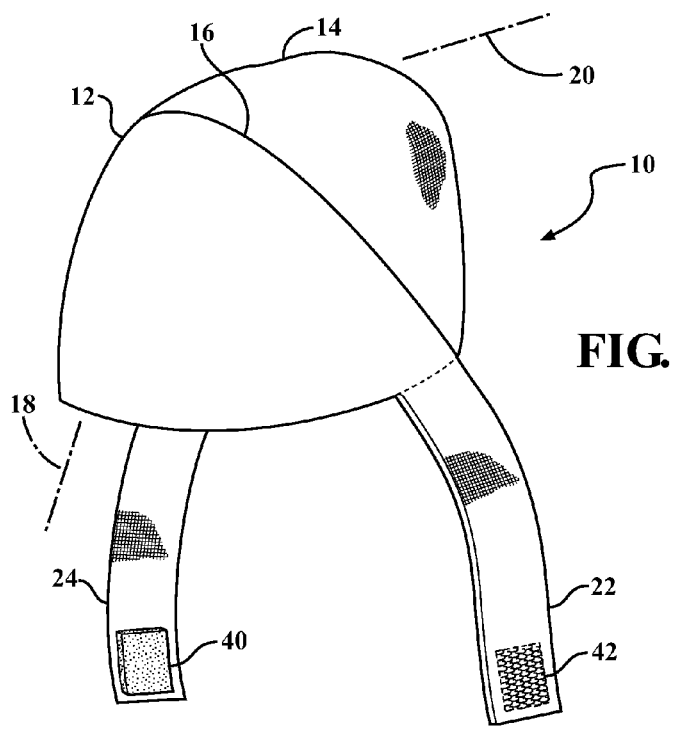
FIG. 1 is a perspective view of one of the two elastic, contoured shoulder caps used with the present invention.

While the present invention may take the alternative forms of a back brace that may be worn over or under everyday clothing, or as a support for a backpack, or as a garment or undergarment having an integrated back brace, all versions of the present invention utilize a shoulder cap, generally indicated at 10. In FIG. 1 the cap 10 is formed of a pair of sections 12 and 14 which are joined together at a line 16. The line 16 may be a sewn or molded seam created between two independent sections of the elastic fabric or the cap 10 may be molded in such a way as to allow it to be formed of an integral elastic fabric section.

Figure 3:
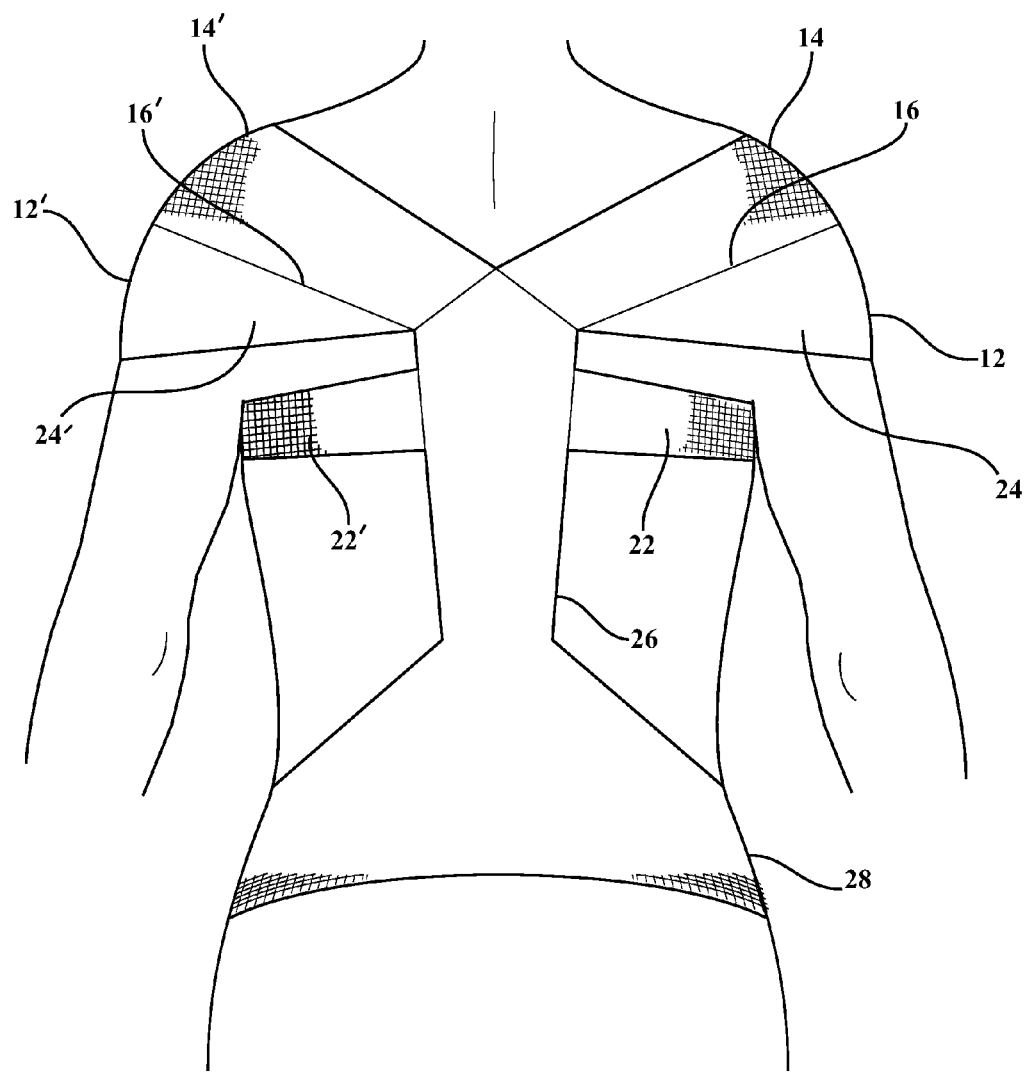
FIG. 3 is a posterior view of an embodiment of the back support employing a spine covering medial strap which may be sewn into an undergarment or may be employed separately with a bottom clip to join to the top of trousers or a normal belt, or built into a backpack.

A posterior view of the back support, as incorporated in an undergarment, is illustrated in FIG. 3. The seam or joint 16 between the two sections 12 and 14 is designed to rest over the acromio-clavicular joint of a shoulder with the section 12 extending generally downward over the top of the humerus bone and with the section 14 extending over the end of the clavicle toward the neck.

To accommodate this fit, the central axes of the two sections, shown as lines 18 and 20 in FIG. 1, are joined at the line 16 or at an obtuse angle to one another which may be in the range of about 100-160 degrees. This allows the two sections 12 and 14 to cap the shoulder with the joint line 16 extending generally over the acromio-clavicular joint.

Figure 2:
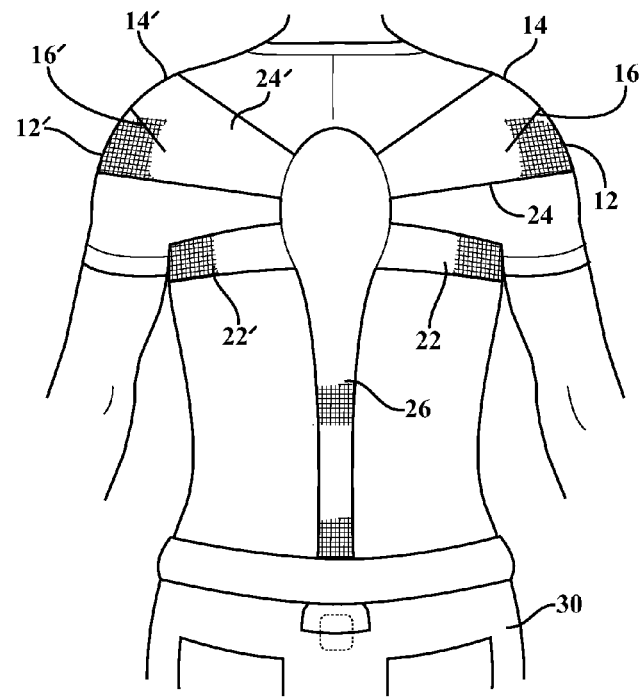
FIG. 2 is a posterior view of a subject wearing the back support/backpack support structure as it would be incorporated in an undergarment.

The anterior section of each of the caps 10 has a lower strap-like extension 22 while the posterior sections of the caps have a strap-like extension 24. As shown in FIG. 2, the strap 22 is adapted to extend under the armpit and the strap 24 extends over the clavicle and generally downwardly on the back. In the posterior views, such as FIG. 3, the strap ends of the cap over the right shoulder are denoted as 22 and 24 while the strap ends of the cap over the left shoulder are denoted as 22' and 24'.

The ends of all four cap straps are secured or formed integrally with the top of a central strap 26 that overlies the wearer's spine. The lower end of the spinal strap 26 is joined to a waist-surrounding strap 28 which preferably rests over the wearer's iliac crest. As shown in FIG. 2, the lower end of the strap 26 may be joined to a belt worn by the user or connected to the top of trousers 30 worn by the user.

Figure 4:
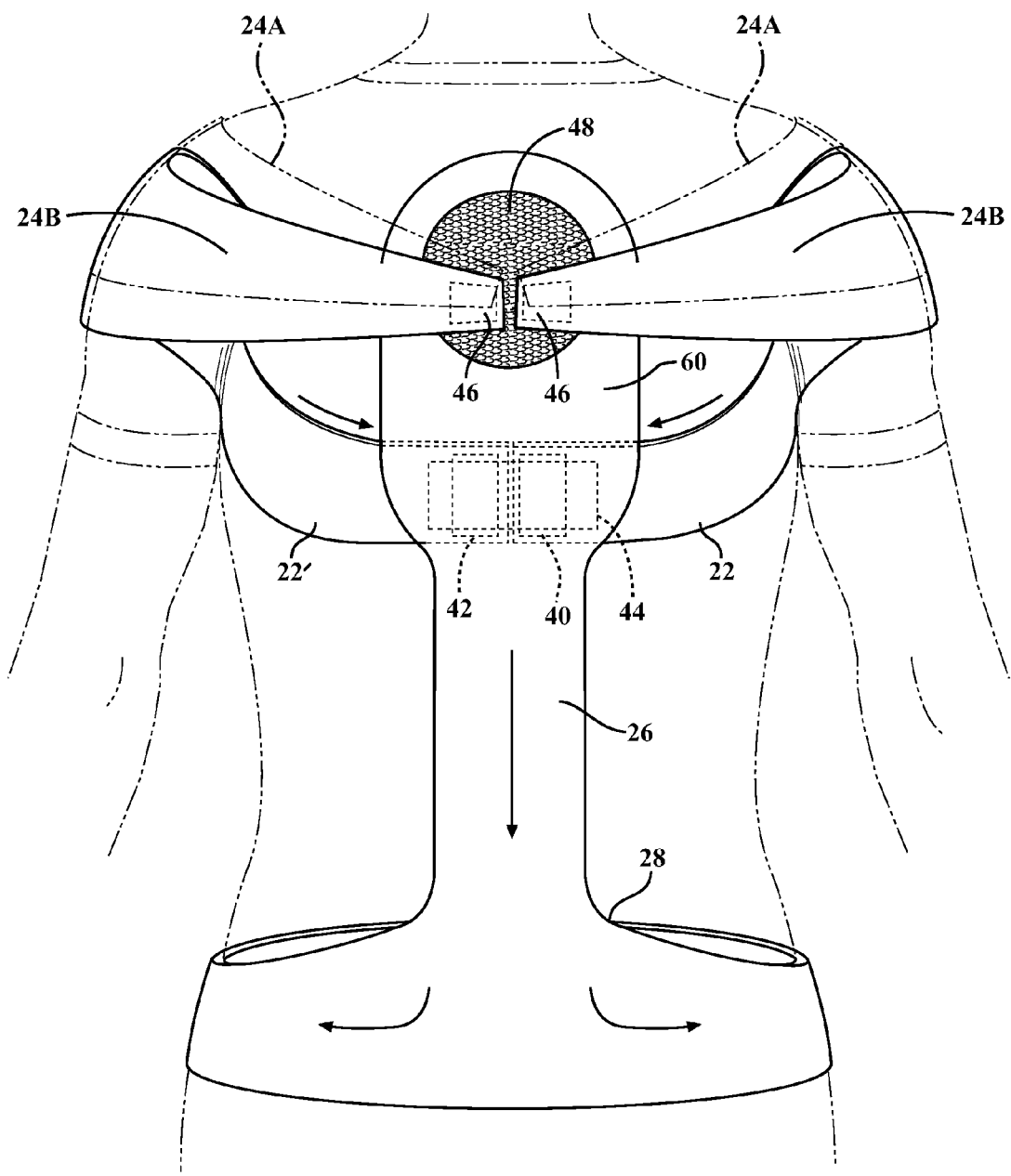
FIG. 4 is a detailed view of an alternative medial adjustable connector for the shoulder cap straps showing alternative angles for the straps from the posterior end of the cap sleeve and showing a medial spine covering strap which terminates at its lower end in a waist-engaging strap.
Figure 5:
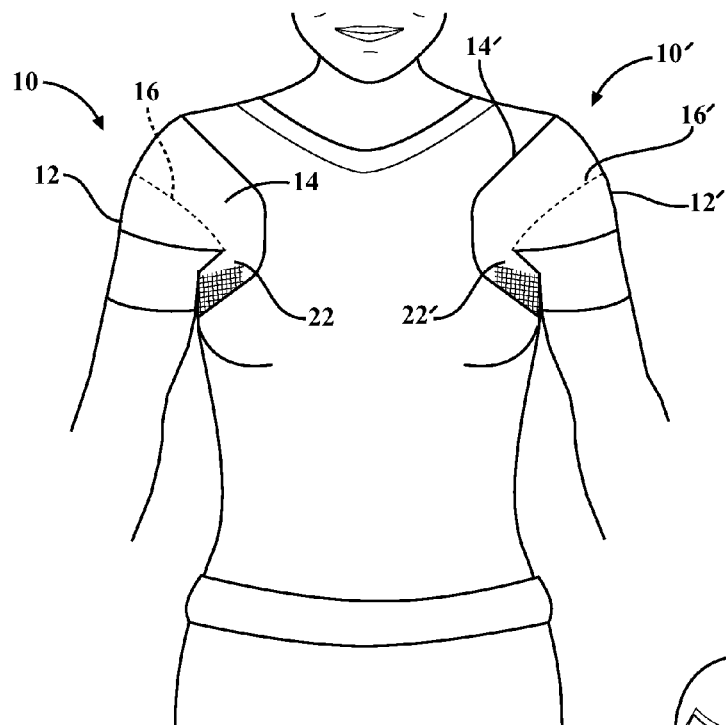
FIG. 5 is an anterior view of the back support structure.

As an alternative to securing the lower end of the spinal strap 26 to a waist-encircling belt 28, as illustrated in FIGS. 4 and 5, FIG. 3 illustrates the posterior view of a strap 26 which is incorporated into a garment or undergarment so that when the garment bottom is secured about the waist of the wearer, the lower end of the strap, which is joined to the lower end of the garment, is drawn toward the user's waist to impose rearward and downward forces on the user's shoulders. In FIG. 2 the strap 26 is illustrated as being clipped to the top of the user's trousers 30. The garment may be a bodysuit so that the joinder between the ends of the straps 22 and 24 is drawn downwardly be the bodysuit fit either with or without a central strap 26.

In all the embodiments, the straps should be formed of material having an elasticity in the range of about 0.02-0.15 Young's modulus. The cap sleeves 10 preferably have slightly less elasticity in the range of 0.08-0.15 Young's modulus. The straps may be elastic only along the axis of their length or they may additionally have a degree of elasticity in a direction normal to their length.

FIG. 4 discloses a rear attachment system, preferably intended for use with the backpack support variety of the present invention, although it may also be used with the posture support. This embodiment incorporates a spine-covering strap 26 which terminates at its lower end at a waist-encircling strap 28. The two posterior ends of the straps 22 and 22' extending from the bottom of the forward side of the two shoulder straps and extending under the armpits of the wearer may be connected to a fastener end 40 secured near the top end of the spine strap 60 in one of several ways. Preferably, the ends of the straps 22 and 22' terminate in hook-and-loop fastener sections 40 and 42 respectively which may be joined to a hook-and-loop fastener section 44 formed on the spine strap 26 slightly below its upper end. The use of hook-and-loop fastener connections for the separable fastener allows the tension on the straps 22 and 22' to be adjusted. The location of the fastener 44 near the top of the spine strap 26 is preferably at the level of the axillas so that the straps 22 and 22' may extend generally horizontally. The straps 24 are preferably joined to the top end of the strap 26, above the fastener section 44 that engages the ends of the straps 22 and 22'. The angular connection between the straps extending from the shoulder caps over the clavicle must be adjusted on an individual basis. Accordingly, two sets of straps 24A and 24B are illustrated. These represent alternative positions for joining the strap to a central fastener 46 formed adjacent the top of the strap 26.

Again, hook-and-loop fasteners 46 could be employed on the ends of the straps 24 to join to a complementary hook-and-loop section 48 formed on the top of the strap 26 which would provide means for adjusting the tension of the straps as well as their angular position on the section 48.

Alternatively, other forms of separable fasteners such as hooks and loops, buttons and buttonholes, or metal clips could be used to join the ends of the straps 22 and 24 to the top of the strap 26.

Figure 6:
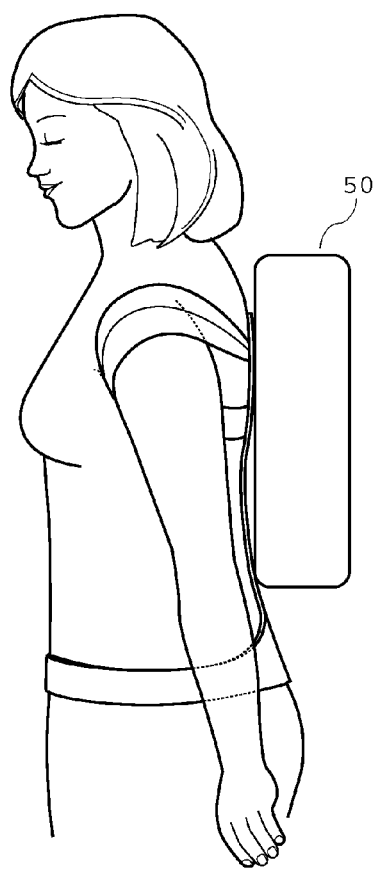
FIG. 6 is a perspective view of an embodiment of the invention incorporated into a combined backpack-posture support.

FIG. 6 illustrates a backpack 50 supported on a set of posture straps of the type illustrated in the other embodiments. The posture straps could be secured to the backpack by sewing or the like or, alternatively, the backpack could be made detachable from the straps through use of separable fasteners of the same type employed in the version of FIG. 4.

In the version of the invention in which the back brace support is integrated into a garment, it may be attached to either the interior or the exterior of the garment. The elastic straps may be secured to the garment along their entire lengths, in which case the garment must have a certain elasticity to allow the brace straps to be placed under proper tension. Alternatively, only the end connections of the straps could be permanently attached to the garment, with slack in the garment fabric to allow the straps to be placed under proper tension to draw the shoulders rearwardly and downwardly.

Having thus described my invention, I claim:

1. A posture support brace comprising:
   a pair of contoured cap sleeves formed of an elastic material shaped to be centered over the acromio-clavicular joints of a user's shoulders, wherein each cap sleeve is formed of a first section and a second section joined together at a seam configured to rest over one of the acromio-clavicular joints of the user with the first section of each sleeve adapted to terminate over an end of the clavicle and the second section of each sleeve extending at an obtuse angle to said first section and adapted to terminate over the top of the humerus bone, the obtuse angle being formed by the central axes of the first section and the second section and being in the range of about 100-160 degrees, with each cap sleeve having an anterior section with a lower end terminating in straps adapted to extend under the respective axillas, and each cap sleeve having a posterior section with a lower end terminating in straps adapted to extend across the user's back, with the ends of each posterior extending strap being joined together at points adapted to rest over the user's spine below the user's neck and drawn toward a central portion of the user's waist by being joined to a top end of a central strap which is adapted to extend over the user's spine and terminates at its top end below the shoulders and at its lower end in a waist strap adapted to rest on the user's iliac crests, the straps being formed of a fabric having elasticity and being supported under tension to urge the shoulders rearwardly and downwardly toward the user's waist to center the user's weight over the user's spine to improve the user's posture.

2. The posture support brace of claim 1, wherein the brace is integrated in a garment and the ends of each strap are drawn toward the user's waist by drawing the waist of the garment under a belt adapted to surround the user's waist.

3. The posture support brace of claim 1, wherein the brace is integrated in a bodysuit and the ends of the straps are drawn toward the user's waist by the fit of the bodysuit.

4. The posture support brace of claim 1, wherein the ends of each of the straps are joined together through separable fasteners.

5. The posture support brace of claim 4, wherein the separable fasteners comprise hook-and-loop sections.

6. The posture support brace of claim 4, wherein the separable fasteners comprise clips.

7. The posture support brace of claim 1, wherein the brace is secured within a garment so that the brace is fitted to the user when the garment is donned.

8. The posture support brace of claim 1, wherein a backpack is secured to the straps so that the backpack is carried on the user's body when the brace is worn by the user.

9. A posture retaining back brace, comprising: a pair of complementary contoured cap sleeves formed of elastic material, shaped to be centered over the two acromio-clavicular joints of a user's shoulders, each sleeve having a first section adapted to terminate over a user's clavicle along a first axis, and a second section adapted to terminate over the top of the humerus bone along a second axis, the two sections being joined together along seam adapted to extend over an acromio-clavicular joint so that the first and second axes form an obtuse angle in the range of about 100-160 degrees, the anterior and posterior sides of each cap sleeve terminating in an elongated strap with the strap on the anterior side being adapted to extend under the user's armpit to the posterior side and the strap on the posterior side adapted to extend over the user's back with the two straps formed on each cap sleeve being secured to points adapted to rest over the user's spine and below the shoulders and neck, the points being at the top end of a central strap adapted to extend over the user's spine and connecting at its lower end to a waist strap, all of the straps of the brace being formed of a fabric having elasticity and all of the straps being sized to be under tension to draw the user's shoulders rearwardly and downwardly toward the user's waist to center the user's weight over the user's spine to improve the user's posture.

10. The posture retaining back brace of claim 9, secured to the interior of a garment so that the user donning the garment is fitted with the brace.

* * * * *